United States Patent [19]

Simo

[11] 3,934,454

[45] Jan. 27, 1976

[54] GAS CONDITIONER AND ANALYZER

[75] Inventor: Stephen G. Simo, Rockland, Mass.

[73] Assignee: Allis-Chalmers Corporation, Milwaukee, Wis.

[22] Filed: Dec. 4, 1974

[21] Appl. No.: 529,349

[52] U.S. Cl. ............................................... 73/29
[51] Int. Cl.² ...................................... G01N 31/00
[58] Field of Search ........ 73/1 R, 23, 27 R, 29, 336, 73/343 R, 344; 137/88, 90, 458; 141/47–49, 63, 64, 83, 92, 94, 95, 192, 231, 286, 383

[56] References Cited
UNITED STATES PATENTS

| | | | |
|---|---|---|---|
| 2,591,760 | 4/1952 | Zaikowsky | 73/27 R |
| 3,234,780 | 2/1966 | Pappas | 73/29 |
| 3,620,265 | 11/1971 | Strople et al. | 141/92 X |
| 3,727,651 | 4/1973 | Biever | 141/231 |

*Primary Examiner*—Richard E. Aegerter
*Assistant Examiner*—Frederick R. Schmidt
*Attorney, Agent, or Firm*—Robert C. Jones

[57] ABSTRACT

A portable unit to maintain the dielectric integrity of the sulfur hexafluoride gas of a gas insulated metal-clad substation system without taking the substation out of service. The gas conditioner and analyzer provides the means for achieving the required control of the insulating gas by providing means for measuring the gas temperature, moisture and pressure, removal of moisture and products of decomposition from the gas, and, if necessary, replenishment of the gas.

7 Claims, 8 Drawing Figures

GAS CONDITIONER AND ANALYZER

BACKGROUND OF THE INVENTION

A gas insulated metal-clad substation system, more commonly referred to as a mini-sub, is an assembly of fluid isolated compartmentalized components whose live parts are contained in and supported by electrically interconnected grounded housings. All live parts are mounted on solid insulators and insulated from their metal housing by pressurized $SF_6$ gas. The unique characteristics of this system pose special requirements, one of which is the control of the condition of the insulating gas. The dielectric integrity of the substation can be adversely affected by contaminants, particularly foreign particles, moisture and products of decomposition of the gas in the modular components. Control of moisture and products of decomposition can be partially achieved through interval molecular sieve materials which absorb the impurities. However, full control of the moisture and products of decomposition has not been possible and necessitates the complete evacuation of the insulating gas resulting in complete outage of the mini-sub.

It is desirable to provide a portable gas conditioner and analyzer which will permit the maintainence of the dielectric integrity of the sulfur hexafluoride insulating gas in a mini-sub without taking the mini-sub out of service.

SUMMARY OF THE INVENTION

In accordance with the preferred embodiment of the present invention, a portable gas conditioner and analyzer is provided to circulate the insulating gas in the mini-sub, monitor the moisture content and temperature and pressure of the circulated gas, remove excess moisture and the products of decomposition from the gas and replenish the mini-sub with make-up gas when necessary.

Accordingly, it is a general object of the present invention to provide an improved novel gas conditioner and analyzer.

A more specific object of the present invention is to provide an improved gas conditioner and analyzer which is portable and particularly adaptable for use with a gas insulated metal-clad substation system that is capable of being used by a single operator.

Another object of the present invention is to provide an improved gas conditioner and analyzer which is capable of sensing and monitoring the moisture content and the temperature of the insulating gas in a mini-sub.

Still another object of the present invention is to provide an improved gas conditioner and analyzer which is capable of circulating the gas in a mini-sub system and filtering contaminants from the gas.

Yet another object of the present invention is to provide an improved gas conditioner and analyzer which includes provision for providing make-up gas to the mini-sub system.

A further object of the present invention is to provide an improved gas conditioner and analyzer which incorporates provisions for protecting a mini-sub system against underpressure and overpressure conditions.

Further objects and advantages of the present invention will become more readily apparent from the following specification taken in conjunction with the accompanying drawings:

DESCRIPTION OF THE PREFERRED EMBODIMENT

Figure 1:
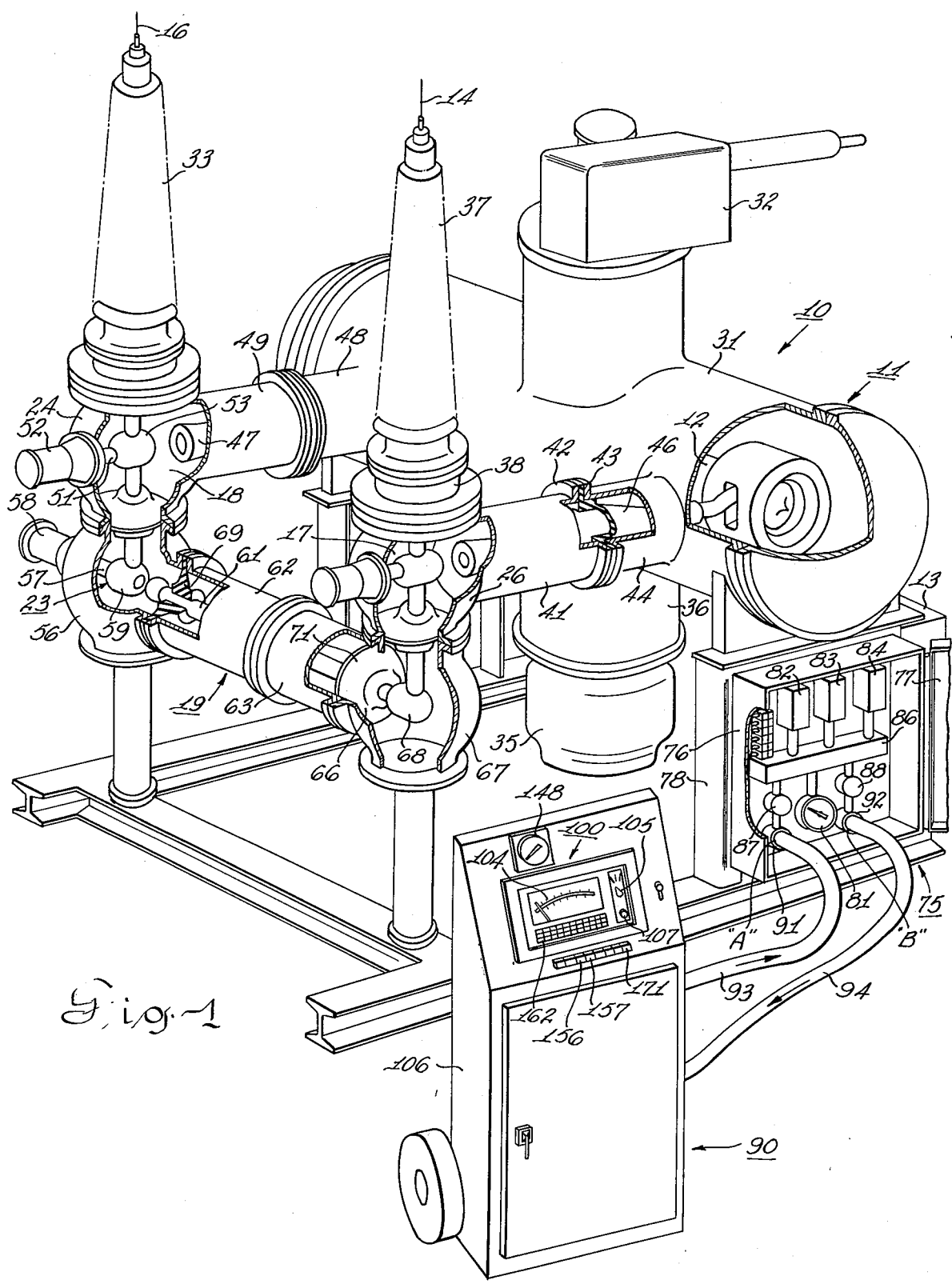
FIG. 1 is a perspective view of a single-phase mini-sub system showing the improved gas conditioner and analyzer connected to a monitoring station of the mini-sub system.

As shown in FIG. 1, a single-phase mini-sub system 10 includes a circuit breaker module 11. The circuit breaker module 11 includes a circuit breaker means 12 which is operatively interposed between a power source and a load via a transmission bus 14 and a load bus 16. The protective arrangement of the circuit breaker means 12 includes a pair of disconnect switches operatively disposed within sealed housings 17 and 18 and which are connected to the transmission bus 14 and the load bus 16, respectively.

In order to service the circuit breaker means 12 without interrupting the circuit between the transmission bus 14 and the load bus 16, a bypass circuit 19 is provided and includes a bypass disconnect switch 23 disposed within a sealed housing. The bypass disconnect switch 23 is connected to the transmission bus 14 at a position to the line side of the disconnect switch housing 24. The opposite terminal of the bypass disconnect switch 23 is connected to the load bus 16 at a position to the load side of the disconnect switch housing 24. Thus, whenever the circuit breaker means 12 requires servicing or inspection, such work can be accomplished without interrupting the circuit to the load bus 16. This is accomplished by closing the bypass disconnect switch in housing 24 thereby establishing a maintaining circuit around the circuit breaker means 12. With the maintaining circuit through the bypass disconnect switch in housing 24 established, the disconnect switches in housings 24 and 26, respectively, may both be opened to thereby isolate the circuit breaker means 12.

The components described above are enclosed in metal housings which are sealed and isolated from each other and which contain insulating medium such as $SF_6$ dielectric gas at a relatively low pressure. The circuit breaker means 12 also uses the $SF_6$ dielectric gas to extinguish the arc drawn between contacts upon the opening of the circuit breaker. The circuit breaker means 12, as well as the centrally disposed supporting housing, is disposed within a tank 31 in which the $SF_6$ dielectric gas is contained at a relatively low pressure. The synchronous operation of the contacts (not shown) of the circuit breaker means 12 is accomplished by an operator 32 connected internally through suitable operating linkage to the contacts.

Gas at a relatively high pressure is contained within a supply tank 35 which is secured in gas-tight relationship to the end of the circular support 36. From the high pressure tank 31, the gas is directed to the central support housing (not show) by means of a supply pipe which has gas-tight fitting relationship with the housing and the supply tank.

The transmission bus 14 is electrically connected to an electrical terminal connector carried at the outer end of a terminal bushing 37 and continues through the terminal bushing 37. Support for the terminal bushing 37 on the transformer housing 38 is afforded by means of a gas-sealed flange-to-flange relationship effected between the lower end of the bushing 37 with the upwardly facing end of the transformer housing 38. The lower flange end (not shown) of the current transformer housing 38 mates with and is bolted in gas-sealed relationship to a top circular flange (not shown) formed on the disconnect switch housing 26. The load bus 16 extends through a terminal bushing 33 which is supported on the associated transformer housing in gas-tight relationship. A gas barrier (not shown) isolates the interior of the bushing 33 from the interior of the housing 24. A cylindrical extension 41 is provided with a circular flange 42 which mates with and is bolted in gas-tight relationship to a circular flange 43 formed on a leftwardly extending cylindrical extension 44 of the circuit breaker tank 31. A sealed relationship between the extension 44 is effected by means of a gas barrier 46 which also operates to isolate the interior of the tank 11 from the extension 41.

At the left end of the circuit breaker 12, an electrical conduit 47 is electrically secured thereto and extends horizontally in coaxial relationship through a horizontal housing extension 48 and through a supporting gas barrier member (not shown) similar to the gas barrier 46 into the grounding switch housing extension 49. The gas barrier (not shown) associated with the extension 48 and 49 operates to isolate the interior of the tank 11 from the disconnect switch housing 24. The electrical continuity continues through the disconnect switch housing 18 via an axially movable contact rod 51 which is actuated by an operator 52. The axial movable contact rod 51 is adapted to move through a bracket 53 into electrical engagement with the contact end of the conductor 47.

As previously mentioned, a bypass circuit 19 is provided for establishing a maintaining circuit around the disconnect switches 17 and 18 whenever the circuit breaker means 12 is out of service for servicing or other reasons. To this end, a bypass disconnect switch 23 is located within a bypass disconnect switch housing 56. The bypass switch 23 includes an axially movable contact rod 57 that is operated by means of an operator 58 through a contact bracket 59 into and out of engagement with the contact end of a conductor 61. With the contact rod 57 in engagement with the contact of the conductor 61, an electrical circuit is established through the disconnect switch 18 to the bypass switch 23 to the conductor 61. The electrical conductor 61 extends through a connecting housing 62 which has sealed engagement with the flanged end of the bypass switch housing 56. Interposed between the intermediate connecting housing 62 there is provided an expansion and contraction housing portion 63 which is longitudinally adjustable in accordance with temperature variations in the environment in which the unit 10 will be located. The expansion and contraction housing portion 63 also serves to provide alignment and tolerance compensation. At its opposite end the expansion housing 63 is secured in sealed relation to an entrance port 66 of a corner housing 67 in which an electrical bracket 68 is contained and to which the conductor 61 is electrically secured. As shown, the conductor 61 is supported within the axially aligned housings 62 and 63 in coaxial relationship by operation of a gas barrier and insulator support 69. A similar arrangement is provided between the end of the expansible housing 63 and the housing 67. To this end, a gas barrier and insulator support 71 is provided and is disposed within the housing 63 at the right end thereof and isolates the interior of the housing 67 from the interior of the housings 62–63.

The circuit breaker module 11 of the mini-sub system 10 is provided with a gas compressor, filters, gauges and pressure switches, all of which are housed within a control cabinet 13 located at the front of the mini-sub system 10. All other compartmentalized components are connected to the gas monitoring station 75. Thus, in a three-phase system, there will be as many monitoring systems or stations 75 as there are isolated compartment components. For example, the single-phase mini-sub system 10 is arranged to have seven individual gas isolated compartments; namely, the bushings 33 and 37, each of the three disconnect switch housings 24, 26 and 56, the bypass circuit housing 62–63 and the corner housing 67. Since a mini-sub installation is normally a three-phase system, each phase will comprise a unit 10. Thus, the similar gas isolated compartments of each phase will be interconnected to a single monitoring station similar to the station 75.

The single-phase mini-sub system 10, shown in FIG. 1, is but one module of a three-phase modular system with all compartment components being interconnected with small diameter tubing (not shown) which are connected to the gas monitoring station 75. The arrangement of the gas tubing (not shown) is such as to permit circulation of the gas to all sections of a given compartment from fittings located in the gas monitoring station 75. As shown in FIG. 1, the gas monitoring station 75 includes a cabinet 76 having a hinged closure door 77. For operator accessability, the cabinet 76 is mounted on the supporting frame 78 of the mini-sub installation. The monitoring station includes a pressure gauge 81 and three pressure switches 82, 83 and 84. The three pressure switches are connected to the various isolated compartments of the mini-sub system 10 via a manifold 86 that is connected to common output and input fluid lines or tubing, previously mentioned. Also included at the monitoring station 75 are a pair of manual valves 87 and 88 which are also connected to the various isolated compartments of the mini-sub via the manifold block 86. Quick-connect couplings 91 and 92 associated with the valves 87 and 88 facilitate the coupling of a gas conditioner and analyzer 90 to the monitoring station 75.

The pressure switch 82 operates as an underpressure sensor and senses the pressure of the gas within the mini-sub system 10. Should the pressure in the particular gas compartment of the mini-sub system drop below a safe operating level, the switch 82 operates as an alarm and also as an isolation switch to trip associated isolating disconnect switches (not shown) and opens the breaker 12.

Switch 83 is an underpressure alarm switch and operates to sense low level pressure and alert personnel whenever the gas pressure in an associated compartment is below a predetermined safe level. On the other hand, switch 84 is an overpressure sensor and operates to alert personnel when the gas pressure in an associated gas isolated compartment is too high.

The monitoring station 75 facilitates the operative connection of the gas conditioner and analyzer to the mini-sub system 10. The connection of the gas conditioner and analyzer 90 to the monitoring station 75 is via a pair of gas hoses 93 and 94 each having male quick-connect couplings. The gas conditioner and analyzer 90 includes a two-stage oil-less pump circulator 96 that has metallic bellows-type pistons. The circulator 96 operates to circulate the gas through the connected compartment or compartments and the gas conditioner and analyzer 90 so that all the gas is conditioned and tested whenever the periodic checks are made. Two filter systems 97 and 98, FIGS. 2, 4 and 6, on the output and input sides of the circulator 96 operate to filter the gas as it is received from an isolated mini-sub compartment and also to filter the gas prior to its being pumped back into the compartment being tested.

Figures 4, 8:
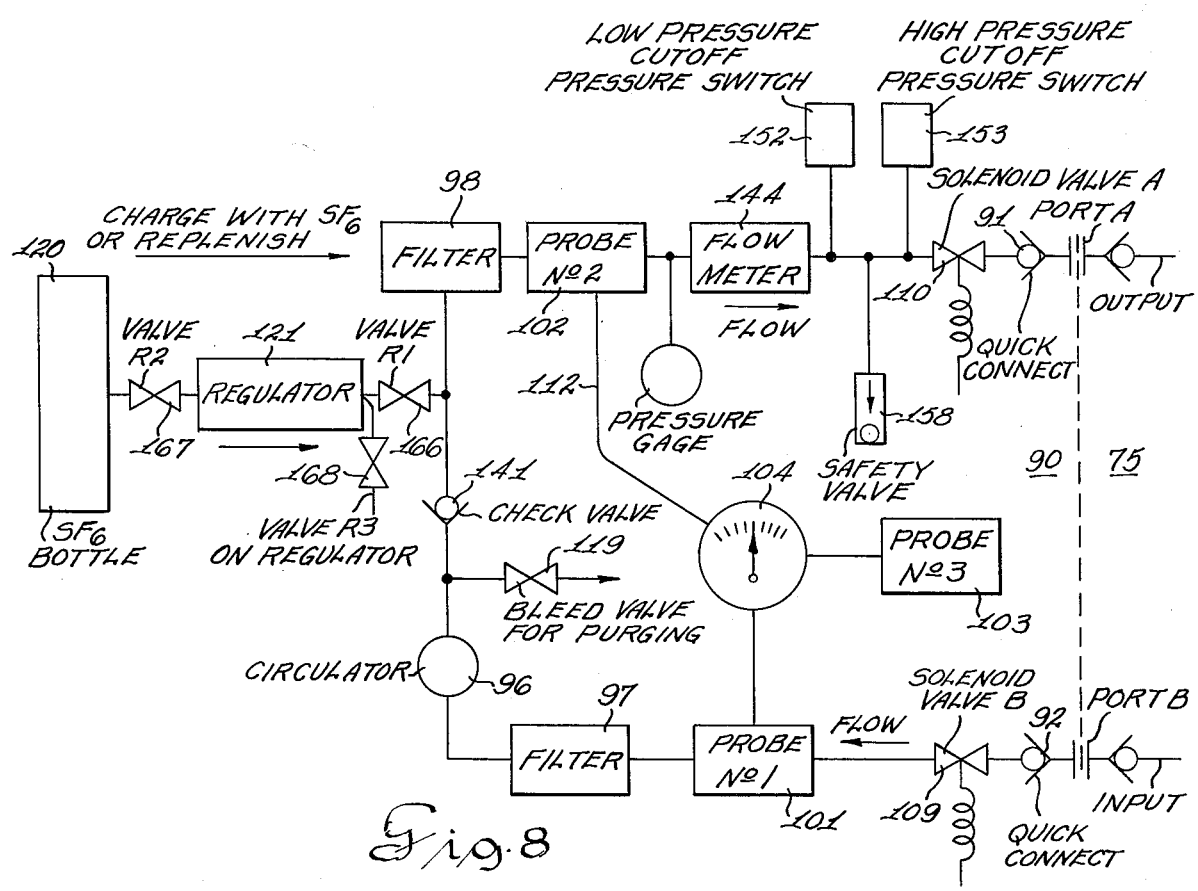
FIG. 4 is an enlarged plan view of the gas conditioner and analyzer with the control panel removed.

A hygrometer-thermometer 100 having three electronic sensor probes, 101, 102 and 103, FIGS. 4 and 8, is an essential component of the gas conditioner and analzyer 90. One probe 101 monitors the moisture content and temperature of the gas at the input side of the gas conditioner and analyzer. Sensor probe 102 monitors the moisture content and temperature of the gas before it is circulated back to the compartment being tested. The third probe 103 is used to measure the gas moisture content of the circuit breaker 11. This can be done by inserting the third probe 103 in a remote sampling manifold (not shown) associated with the circuit breaker and located in the control cabinet 13. The hygrometer is based on an aluminum oxide capacitor, the impedance of which changes as a function of vapor pressure. Its impedance is insensitive to gas temperature or flow rate. Thus, it can be used to measure moisture in a flowing or a static gas. The sensitivity of the hygrometer is such that moisture concentrations from 10 to 3000 parts per million by volume can be measured. The temperature sensor utilizes a thermistor as a transducer.

Sensor probes 101, 102 and 103 are selectively read on the meter 104 by means of a selector switch 105 located on the console panel. Thus, by positioning the selector switch to position 1, the sensor probe 101 is connected into the circuit of the meter 104. Similarly, position 2 connects probe 102 into the circuit while position 3 connects probe 103 into the meter circuit.

A common meter 104, marked with both moisture and temperature scales on the gas conditioner and analyzer cabinet 106, provides a readout for these functions. A spring biased switch 107 normally inserts the meter 104 in the hygrometer circuit and is actuated to read the temperature.

Figure 2:
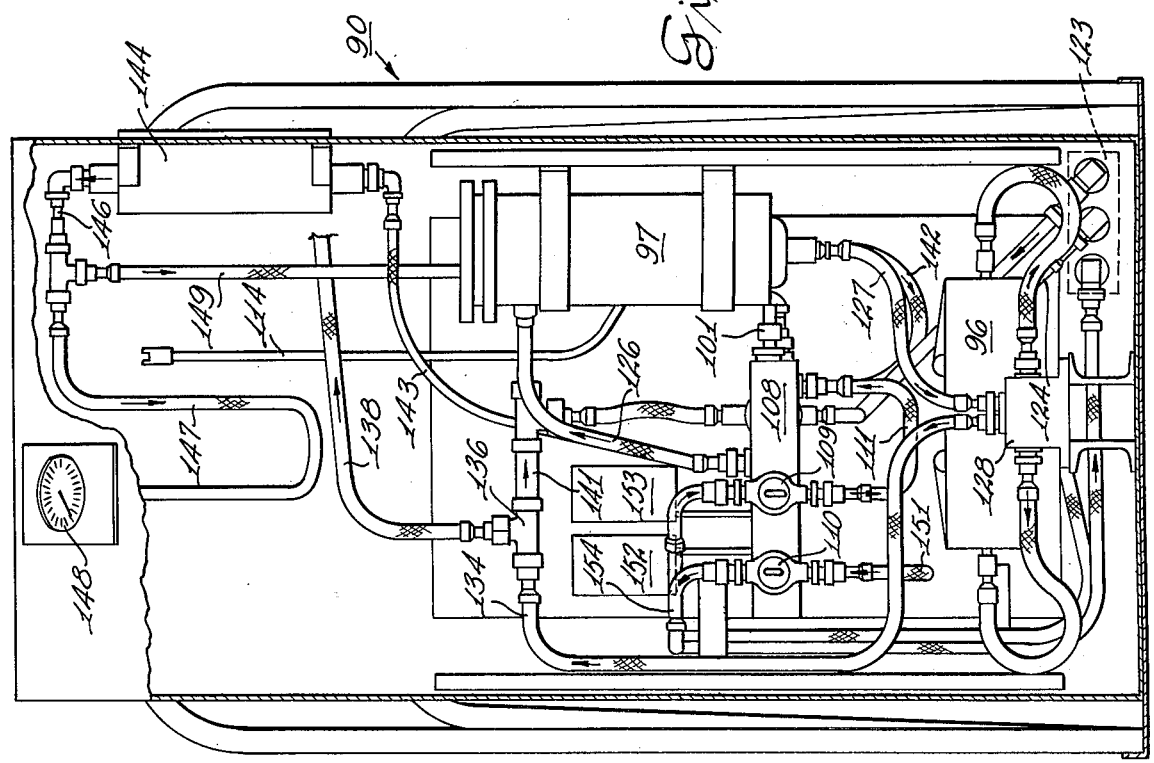
FIG. 2 is an enlarged front view of the gas conditioner and analyzer with the access door and control panel removed to show the various components.

To this end, a sampling manifold 108 receives the probes 101 and 102 as depicted in FIGS. 2 and 4. The probes 101 and 102 are similar and the arrangement of the probe 101 will also apply to probe 102. As shown in FIGS. 2 and 4, the probe 101 is inserted within a suitable chamber in the manifold 108 and is at a right angle relative to the in-flowing gas that is directed to the manifold from the solenoid valve 109 via a connecting line 111. The probe 101 is electrically connected to the meter 104 via a cable 112 that includes a plug-in terminal end 114 compatible with a receptacle (not shown) on the meter 104, as shown in FIGS. 6 and 7.

Figure 6:
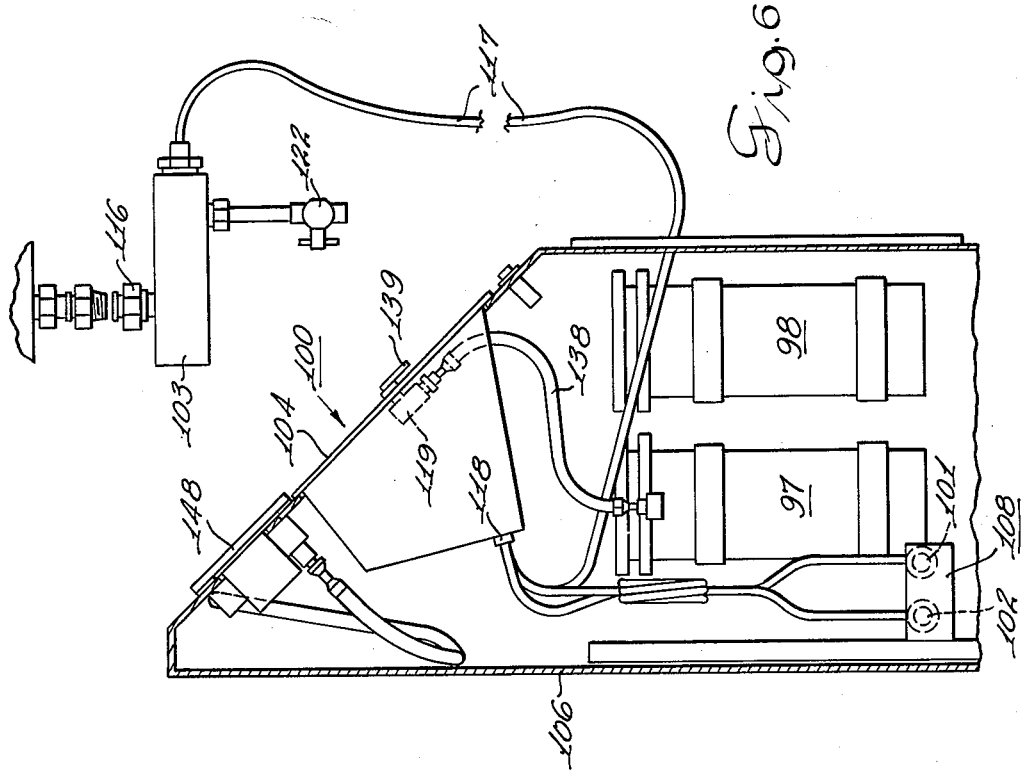
FIG. 6 is an enlarged left side view of the gas conditioner and analyzer of the upper portion thereof with parts deleted to show the meter and sensor probes.
Figure 7:
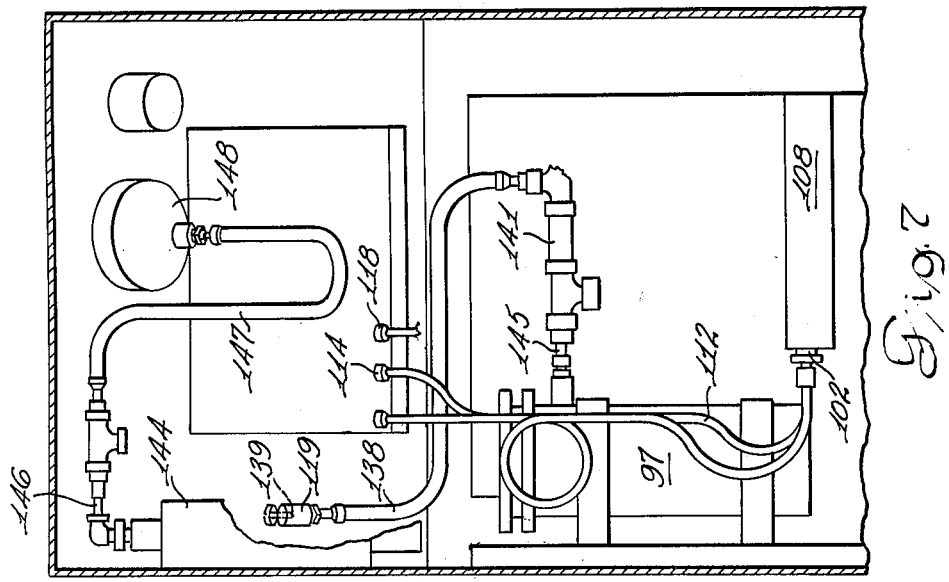
FIG. 7 is an enlarged rear view of the gas conditioner and analyzer with parts deleted to show the meter and sensor probes connected thereto; and, FIG. 8 is a schematic representation of the improved gas conditioner and analyzer of the present invention connected to a mini-sub.

The probe 103, FIG. 6, includes a fitting 116 which is connectable to the remote circuit breaker sampling manifold (not shown) located in the control cabinet 13. Thus, the gas sample from the circuit breaker will impinge the elements of the sensor 103 at right angles thereto. The sensor 103 is electrically connected to the meter 104 by an extra length cable 117 which includes a plug-in terminal 118 similar to the plug-in terminal 114. The sensor 103 is also provided with its own manual operable purging valve 122. With this arrangement, gas temperature and moisture content can be measured directly at a monitoring station on the equipment or at a circuit breaker without circulating the gas.

The gas conditioner and analyzer includes a tank of compressed gas 120 and a regulator 121 that is used to replenish gas when needed.

Figure 3:
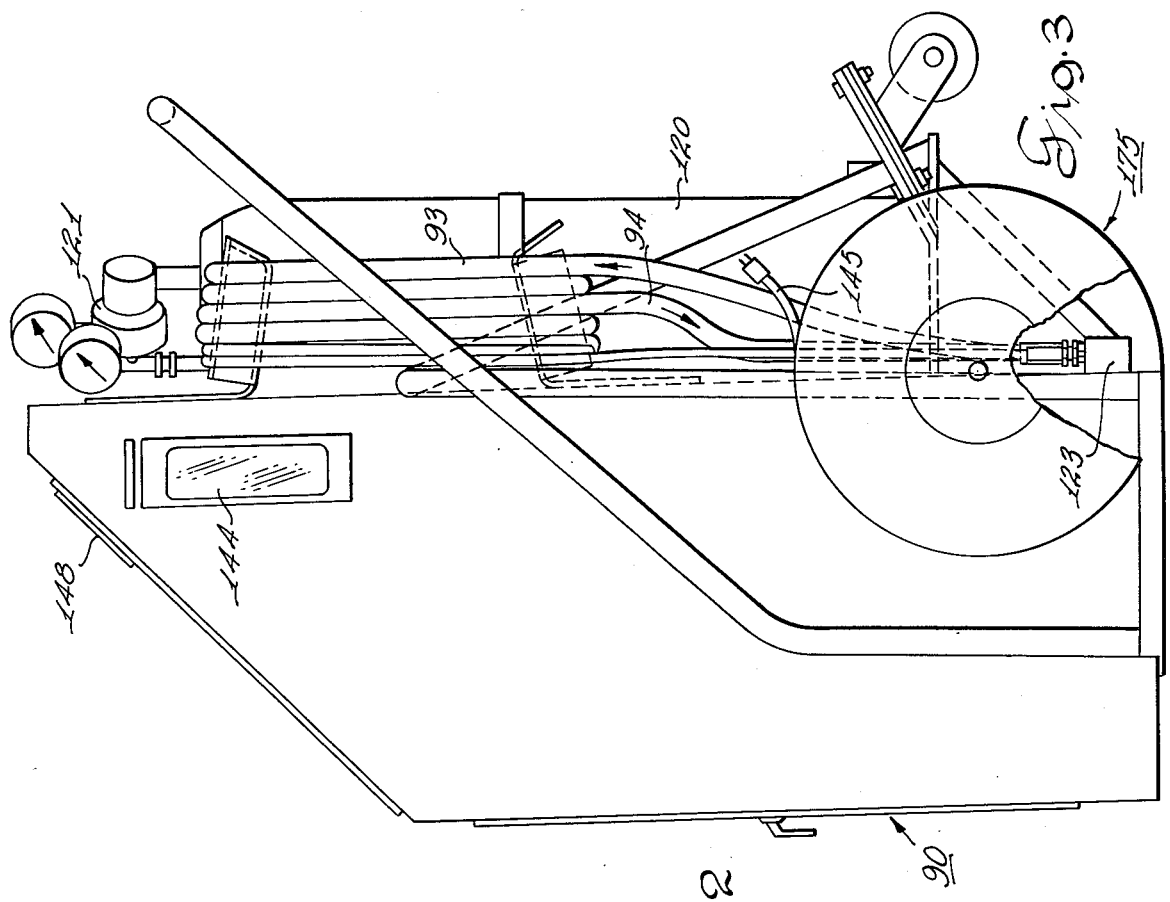
FIG. 3 is a view in right side elevation of the gas conditioner and analyzer showing the storage tank and hoses.

The interrelationship of the gas conditioner and analyzer 90 components is illustrated schematically in FIG. 8. Solenoid valves 109 and 110 on the manifold 108 are opened automatically when the gas conditioner and analyzer is at normal pressure and electrically energized. When the circulator 96 is energized, the gas is circulated from port "B" of the monitoring station 75, to which the hose 94 is connected, into the gas conditioner and analyzer 90 through a manifold 123, shown in FIGS. 2, 3 and 5. From the manifold 123, the gas flow is directed via a connecting line 124 to the solenoid valve 109. The gas then flows through the solenoid valve 109 into the chamber of the manifold 108 in which the sensor probe 101 is located and the temperature and moisture content of the incoming gas is measured. The flow of gas continues from the probe 101 manifold chamber through the incoming filter 98 via a connected line 126. The gas flows through the filter 98 and via a line 127 into a distribution manifold 128. From the distribution manifold 128, the gas is directed to both ends of the circulator 96 via connection lines 129 and 131. The output sides of both ends of the circulator 96 are directed back to the distribution manifold 128 via lines 132 and 133. The gas from the circulator 96 flows via a line 134 through a tee 136 to which the purge valve 119 is connected via a line 138. In FIG. 2, the line 138 is not shown connected to the purge valve 119 but terminates in the area in which the valve is located. The valve 119 is shown in FIGS. 6 and 7, and its actuating handle 139 is shown located on the console 106. The gas flow continues through the tee 136 and through a check valve 141 and flows into the outgoing filter 97 via the connecting line 145. From the bottom of the outgoing filter 97, the gas continues to flow through a line 142 to a chamber in the manifold 108 in which the sensor probe 102 is located. The line 142 is connected to communicate with the chamber in which the probe 102 is located in a manner that the in-flow of gas into the chamber impinges the sensing elements of the probe 102 at a right angle. The condition of the gas to the probe 102 is monitored by the probe and read on the meter 104. The monitored outgoing gas flowing through the manifold 108 and through internal passages (not shown) flows into a connected line 143, the opposite end of which is connected to a flow meter 144. From the flow meter 144, the gas flows through a connected line 146 and into a pressure gauge line 147 to a pressure gauge 148. The gas flow from the flow meter 144 also is directed into a line 149 and thence back to the manifold 108. The gas flow from the line 149 is directed into a connected line 151 which is connected to the inlet side of the solenoid valve 110. As the gas flows within the internal passage (not shown) in the manifold 108 to the valve 110, the pressure is monitored by a low pressure cutoff pressure switch 152 and the high pressure cutoff pressure switch 153 which are connected to the internal flow passage in the manifold 108. From the solenoid valve 110, the gas is directed via a connecting line 154 to the manifold 123 and thence into the hose 93. The hose 93 is connected to port A of the gas monitoring station 75.

The pressure gauge 148 in the output line can be used to check the accuracy of the gauge 81 on the mini-sub. The flow meter 144 is also utilized to calculate the time it takes to complete a volumetric change of a gas compartment 10. The total volume of the compartment is indicated on the gas compartment nameplate (not shown) and by multiplying the volume by the reciprocal of the flow rate the gas conditioner and analyzer, the operator knows how long to run the gas conditioner and analyzer for one complete volumetric change. The operator also knows how many volumetric changes it takes to bring the gas compartment down to an acceptable moisture level. This type of information is of value to an operator in a gas insulated circuit breaker arrangement of complex gas chambers connected in series compressing compartment. Thus, flow meter 144 monitors the output flow providing a check on the performance of the circulator 96 and serves to guide the fillrate when the system is being replenished from the gas conditioner and analyzer gas bottle 120. The low pressure cutoff switch 152 and the high pressure cutoff switch 153 are connected in the output line to close valves 109 and 110 automatically in the event of underpressure or overpressure. These switches also energize warning lights 156 and 157 on the control panel of the cabinet 106. A safety valve 158 is connected into the manifold output passage and vents gas to the atmosphere in the event of extreme overpressure to protect the gas conditioner and analyzer components. The check valve 141 assures proper direction of gas flow when the gas conditioner and analyzer is being purged before use and during gas replenishment.

Figure 5:
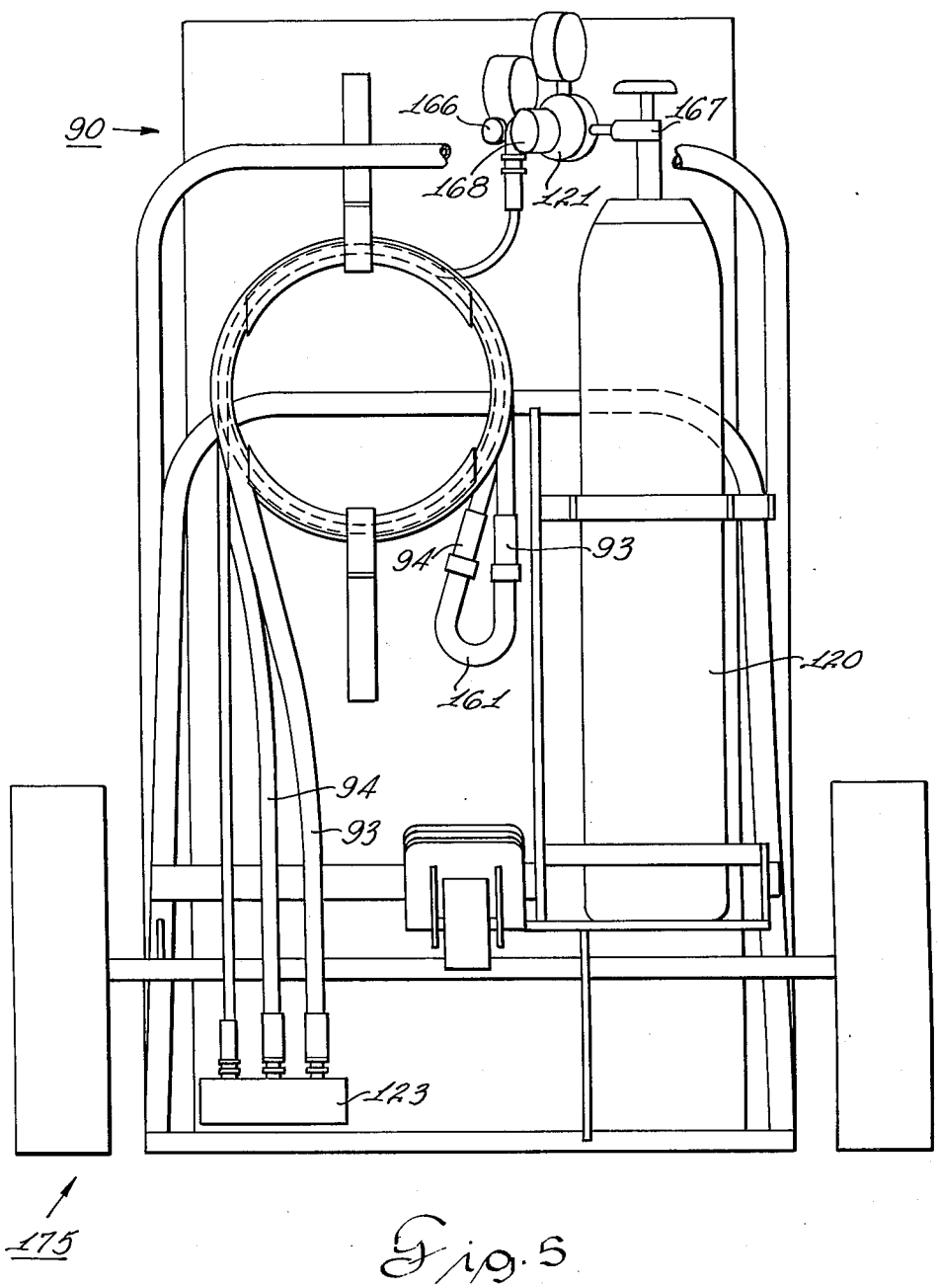
FIG. 5 is a view in rear elevation of the gas conditioner and analyzer.

In operation, before the gas conditioner and analyzer 90 is connected to a mini-sub, a "short circuiting" hose 161, FIG. 5, is connected across the hoses 93 and 94 and the unit is filled from its own gas bottle 120. The purge valve 119 is opened long enough to assure that air and moisture are vented from the unit. The pressure of the gas in the gas conditioner and analyzer is adjusted to approximately that of the equipment to be monitored. Power is supplied to the gas conditioner and analzyer via the plug-in cord 145, and gas is circulated within the unit to assure that all impurities are removed by the filters. The "short circuiting" hose 161 is removed when the gas conditioner and analyzer is to be connected to the gas monitoring station 75. The gas conditioner and analyzer is maintained in the purged and pressurized state by means of the quick-connect two-way check valve couplings 91 and 92. Connections are then made to the respective mating quick-connect couplings on the gas monitoring station 75. When manual valves 87 and 88 in the gas monitoring station 75 are opened, a check of the under and over pressure alarm lights 156 and 157 and the pressure gauge 148 is made to assure that all components are in operating order. The circulator 96 is energized to pump gas from the mini-sub 10 through the gas conditioner and analyzer 90. The temperature readings, as indicated on the scale 104, should be less than 50°C. above ambient, the actual level depending on load conditions and incident radiation.

Moisture readings should be well below the concentrations which will give condensation (dew point) at the lowest expected ambient temperature to which the mini-sub will be exposed. The meter reading can be converted to dew point in degrees Centigrade or degrees Fahrenheit with a conversion table 162 on the face of the console.

The remote sampling probe 103 can be used by attaching it directly to the sampling manifold of the circuit breaker as previously mentioned or to a gas monitoring station 75. The procedure for readout is the same as previously outlined except that the gas is not circulated through the gas conditioner and analyzer 90.

The requirement for filtering the gas normally occurs because the moisture in the gas has risen to a prohibited level. The procedure for filtering is essentially the same as for circulating the gas through the gas conditioner and analyzer for measurement. During a typical test run, the filters 97 and 98 lowered the moisture content in a test chamber representing a substation gas compartment from 4,000 to 125 parts per million per volume in approximately 7 hours. Filtration of the gas may also be necessary to remove products of gas decomposition. A build-up of such products can occur if disconnect switches are used frequently for interrupting capacitance current; that is, bus charging current or transformer magnetizing currents.

Replenishing the gas system becomes necessary when the gas density falls below 95% of the level stated on the nameplate of the equipment. With the hoses 93 and 94 connected for gas circulation and a valve 166 closed, a valve 167 is opened and valve 168 on the regulator 121 is adjusted to the proper pressure for delivery of gas, approximately 5 lbs. per square inch above the rated pressure. Solenoid valve 110 in the gas conditioner and analyzer 90 and manual valve 87 in the monitoring unit of station 75 must be opened. Gas can then be transferred to the substation compartment by opening valve 166. It is important to adjust the regulator valve for a safe rate of transfer and to allow the gas temperature in the compartment to stabilize before "topping off" to avoid overfilling the equipment.

The gas conditioner and analyzer 90 is designed to provide protection against both underpressure and overpressure conditions. An excessive drop in pressure activates the underpressure switch 152 to de-energize the circulator 96 and close the solenoid valve 109 and 110. This isolates any leaks within the gas conditioner and analyzer from the substation to assure continuous station operation. After correction of the problem and replenishing the gas in the gas conditioner and analyzer, operation can be restored by depressing an underpressure reset button 171 on the console to reenergize the control circuit. The overpressure protection system operates in a similar manner. The overpressure relief valve or safety valve 158 protects the units against extreme overpressures by venting gas to the atmosphere.

The gas conditioner and analyzer 90 is mounted on a lightweight two wheel dolly 175 which facilitates transporting the gas conditioner and analyzer 90 to a mini-sub installation in subcellars or buildings in congested areas.

It is apparent that the gas conditioner and analyzer herein depicted and described is an important and versatile compact auxiliary for increasing the reliability and reducing the maintenance costs of gas insulated metal-clad substations.

The embodiments of the invention in which an exclusive property is claimed are defined as follows:

1. A portable gas conditioner and analyzer for gas insulated substations comprising:
   a two wheeled cart having handle means for facilitating the handling of the gas conditioner and analyzer by a single operator;
   a cabinet mounted on said cart;
   a gas circulator having an inlet side and an outlet side mounted within said cabinet;
   an inlet gas circuit means connected to the inlet side of said gas circulator, said inlet gas circuit means being connectable to the gas insulated substation to provide a gas flow circuit between the substation and said circulator;
   an outlet gas circuit means connected to the outlet side of said circulator, said outlet gas circuit means being connectable to the gas insulated substation to complete a closed gas circuit;
   a first electronic sensor connected to said inlet gas circuit means operable to monitor the moisture content and the temperature of the gas as it flows from the gas insulated substation to said circulator;
   a second electronic sensor connected to said outlet gas circuit means operable to monitor the moisture content and the temperature of the gas as it flows from said circulator to the gas insulated substation;
   a first gas filter in the inlet gas circuit means, said first gas filter being operably disposed to filter the gas prior to said gas flowing to said circulator and after said gas is monitored by said first monitoring means;
   a second gas filter in the outlet gas circuit means, said second gas filter being operably disposed to filter gas directly after the gas leaves said circulator;
   a hygrometer-thermometer supported in said cabinet and having a moisture indicating scale and a temperature indicating scale including a switch normally positioned to connect said hygrometer-thermometer to indicate on one of said scales, said switch being operable when actuated to another position to connect said hygrometer-thermometer to indicate on the other of its scales; and,
   individual means operably connecting said first and second electronic sensors to said hygrometer-thermometer.

2. A portable gas conditioner and analyzer for gas insulated substations comprising:
   a wheeled cart;
   a cabinet mounted on said cart;
   a gas circulator having an inlet side and an outlet side mounted within said cabinet;
   an inlet gas circuit means connected to the inlet side of said gas circulator, said inlet gas circuit means being connectable to the gas insulated substation to provide a gas flow circuit between the substation and said circulator;
   an outlet gas circuit means connected to the outlet side of said circulator, said outlet gas circuit means being connectable to the gas insulated substation to complete a closed gas circuit;
   an inlet solenoid valve connected in said inlet gas circuit means and normally operable to permit gas flow therethrough, said inlet solenoid valve being operable when actuated to block the flow of gas therethrough;
   an outlet solenoid valve connected in said outlet gas circuit means and normally operable to permit the gas flow therethrough, said outlet solenoid valve being operable when actuated to block the flow of gas therethrough;
   a low pressure cutoff pressure switch operably connected in said outlet gas circuit means to sense the pressure of the gas flowing in said outlet gas circuit means, said low pressure cutoff pressure switch being operably connected to said inlet and outlet solenoid valves to automatically actuate said inlet and outlet solenoid valves to block the flow of gas when the pressure of the gas is below a predetermined value;
   a high pressure cutoff pressure switch operably connected in said outlet gas circuit means to sense the pressure of the gas flowing in said outlet gas circuit means, said high pressure cutoff pressure switch being operably connected to said inlet and outlet solenoid valves to automatically actuate said valves when the pressure of the gas flowing in said outlet gas circuit means exceeds a predetermined value;
   a first electronic sensor connected to said inlet gas circuit means operable to monitor the moisture content and the temperature of the gas as it flows from the gas insulated substation to said circulator;
   a second electronic sensor connected to said outlet gas circuit means operable to monitor the moisture content and the temperature of the gas as it flows from said circulator to the gas insulated substation;
   a first gas filter in the inlet gas circuit means, said first gas filter being operably disposed to filter the gas prior to said gas flowing to said circulator and after said gas is monitored by said first electronic sensor;
   a second gas filter in the outlet gas circuit means, said second gas filter being operably disposed to filter gas directly after the gas leaves said circulator;
   a hygrometer-thermometer supported in said cabinet and having a moisture indicating scale and a temperature indicating scale including a switch normally biased to connect said hygrometer-thermometer to indicate on one of its scales, said switch being selectively actuatable to connect said hygrometer-thermometer to indicate on the other of its scales; and,
   individual means operably electrically connecting said first and second electronic sensors to said hygrometer-thermometer.

3. A gas conditioner and analyzer according to claim 2 wherein there is provided a pressure gauge operably connected into the outlet gas circuit means to indicate the pressure of the gas flowing in said outlet gas circuit means; and and,
   a flow meter operably connected to monitor the flow of gas in said outlet gas circuit means.

4. A portable gas conditioner and analyzer according to claim 3 wherein said wheeled cart is a two-wheel vehicle having handle means for facilitating the handling of the gas conditioner and analyzer by a single operator.

5. A portable gas conditioner and analyzer according to claim 4 wherein there is provided a bottle of compressed gas carried on said wheeled cart;
   gas circuit means connecting said bottle of compressed gas to said outlet gas circuit means;
   a regulator in said gas conducting means to regulate the pressure at which gas from said bottle to said outlet gas circuit means is delivered; and,
   a valve interposed in said gas circuit means between said bottle of compressed gas and said outlet gas circuit means to block the flow of gas from said bottle to said outlet gas circuit means, said valve being operable to permit gas flow therethrough.

6. A portable gas conditioner and analyzer according to claim 5 wherein there is provided a check valve in the outlet gas circuit means to prevent back flow of gas to said circulator.

7. A portable gas conditioner and analyzer according to claim 6 wherein said compressed gas in said bottle is sulfur hexafluoride; and,
   there is provided means operable to connect said bottle to said gas conditioner and analyzer in a closed system arrangement to purge and maintain the gas conditioner and analyzer charged with said sulfur hexafluoride gas.

* * * * *